United States Patent [19]
Goldrath

[11] Patent Number: 5,503,626
[45] Date of Patent: Apr. 2, 1996

[54] FLUID DELIVERY SYSTEM FOR HYSTEROSCOPIC SURGERY

[75] Inventor: Milton H. Goldrath, Franklin, Mich.

[73] Assignee: BEI Medical Systems, Hackensack, N.J.

[21] Appl. No.: 239,770

[22] Filed: May 9, 1994

Related U.S. Application Data

[63] Continuation-in-part of Ser. No. 227,724, Apr. 14, 1994, Pat. No. 5,437,629.

[51] Int. Cl.⁶ .................................................. A61M 31/00
[52] U.S. Cl. ............................... 604/65; 604/31; 604/27; 604/48
[58] Field of Search .................... 604/113, 8, 9, 604/19, 21, 27, 28, 29, 30, 31, 35, 39, 47, 48, 54, 55, 65, 66, 67, 80, 81, 93, 131, 279, 329, 330; 128/750, 761, 762, 765, 766, 768, 769, 4, 6, 831, 830

[56] References Cited

U.S. PATENT DOCUMENTS

| | | | |
|---|---|---|---|
| 4,795,424 | 1/1989 | Burner | 128/4 |
| 4,922,902 | 5/1990 | Wuchinich et al. | 604/27 |
| 5,152,746 | 10/1992 | Atkinson et al. | 604/31 |
| 5,178,606 | 1/1993 | Ognier et al. | 604/31 |
| 5,242,390 | 9/1993 | Goldrath | 604/28 |
| 5,320,091 | 6/1994 | Grossi et al. | 128/4 |

*Primary Examiner*—Corrine M. Maglione
*Assistant Examiner*—N. Kent Gring
*Attorney, Agent, or Firm*—Gifford, Krass, Groh, Sprinkle, Patmore, Anderson & Citkowski

[57] ABSTRACT

An open loop system for delivering fluid during hysteroscopic surgery. The system includes first and second fluid conduits in fluid communication with the uterine cavity of a patient. First and second measuring devices are provided for measuring the amount of fluid flowing into and out of the uterus. The measuring devices produce electronic signals which are communicated to a controller which uses them to calculate a value reflecting the difference in in-flow and out-flow. This difference is then compared with a preset value; if the preset value is exceeded, the surgeon knows the patient is absorbing too much fluid, and the procedure may be terminated.

13 Claims, 2 Drawing Sheets

FLUID DELIVERY SYSTEM FOR HYSTEROSCOPIC SURGERY

CROSS REFERENCE TO RELATED APPLICATIONS

This is a continuation-in-part of application Ser. No. 08/227,724, filed Apr. 14, 1994 and now U.S. Pat. No. 5,437,629.

FIELD OF THE INVENTION

The present invention concerns the field of hysteroscopic surgery performed in conjunction with delivery of fluid to the uterine cavity, and more particularly, to a system for delivering said fluid.

BACKGROUND OF THE INVENTION

U.S. Pat. No. 5,242,390 discloses a method and apparatus for thermally ablating the lining of the uterus (known as the endometrium). The patented apparatus comprises a hysteroscope having a proximal portion for insertion into the uterus through the vagina, and a distal, gripping, visualization portion. The hysteroscope comprises both optical means for viewing the uterine cavity and channel means for delivering tissue-coagulating, controllably heated liquid into the cavity, as well as thermal insulation means for the hysteroscope. The thermal insulation means insulates the other body structures from the potentially damaging heat of the liquid during the period of the heated liquid transport and the coagulating surgery with the liquid so as to avoid thermal damage to tissue other than the endometrial tissue (such as vaginal tissue and endocervical tissue). The apparatus also includes liquid supply means into and form the uterine cavity, and control means for regulating the temperature and pressure of the heated liquid.

The method of the patent as described therein includes the steps of: (a) distending the uterine cavity with a physiologically compatible aqueous solution (such as saline solution or other suitable liquid) under direct vision by means of a hysteroscope having channel means for delivering and introducing liquid to the uterine cavity under pressure sufficient to inflate and directly expose the entire endometrial surface; (b) confirming that the proximal portion of the hysteroscope is properly located within the uterine cavity by appropriate visualization of its internal architecture; (c) withdrawing the aqueous solution form the uterine cavity, thus causing it to become substantially collapsed; and (d) distending the thus collapsed uterine cavity under direct vision by means of said hysteroscope by delivering and introducing to the uterine cavity aqueous carbohydrate solution (or a suitable equivalent solution) heated to an endometrial tissue-coagulating temperature under pressure sufficient to directly expose the entire endometrial surface and for a time sufficient to keep the heated solution in contact with the entire surface and, thereby, cause uniform and complete destruction of the endometrium.

The patent discloses a liquid supply means to the hysteroscope in the form of a syringe barrel and plunger containing heated liquid which is manually injected into the inlet port of the hysteroscopic sheath. The fluid which exits out of the uterine cavity and back through said channel and port of the sheath is circulated into a waste reservoir. Optionally, a separate supply of cold liquid is available, also in the form of a syringe barrel and plunger. Various valves are disclosed to control the ingress and egress of the various liquids.

It is also known to perform certain endoscopic procedures on the uterus which involve the circulation of a fluid thereinto for visualization purposes. In order for the surgeon to keep a clear field of view, the circulating fluid must remain free of blood and other loose body tissues which typically accompany such surgery.

Certain problems can arise during such surgical procedures, particularly if the patient absorbs a quantity of the liquid into her circulation (or fallopian tubes) during the installation of the solution. In some types of hysteroscopic procedures, patients have been known to absorb large quantities of the liquid (as much as 2,000 or 3,000 cc) which can cause serious complications, up to and including death. Obviously, it is extremely important to closely monitor the amount of liquid being used to perform these procedures in order to ensure that no significant amounts are being absorbed. The fluid delivery system disclosed in U.S. Pat. No. 5,242,390 does not really provide any practical way of performing such monitoring.

In co-pending application Ser. No. 08/227,724, now U.S. Pat. No. 5,437,629, the present invention has proposed to solve the problem of monitoring the circulating fluid by providing a closed loop conduit including a chamber with graduated marking through which the circulating fluid passes. The chamber can be optically monitored to see if the fluid level remains constant; if not, the procedure can be terminated.

The system described in the co-pending application is particularly well adapted to the delivery of fluid used to perform endometrial ablation or sterilization. However, a closed loop system cannot always be used for fluid delivery for other types of hysteroscopic procedures since the recirculating fluid quickly becomes contaminated with blood and other loose tissue which cannot be removed in any practical way.

SUMMARY OF THE INVENTION

The present invention has been designed to overcome the prior art deficiencies noted above. Accordingly, the invention provides an open loop system for delivering liquid used to perform hysteroscopic procedures involving the uterine cavity, wherein the amount of liquid in use can be closely monitored at all times.

In its broadest aspect, the invention included first and second fluid conduits for, respectively, delivering and drawing away first and second streams of physiologically compatible fluid into and out of the uterine cavity of a patient. The system includes means for measuring the magnitude of said first and second streams (by "magnitude" is meant flow rate, pressure, volume, weight, or any other measurable quality that reflects the quantity of fluid being introduced), and for sending first and second electrical signals indicative thereof. The system also includes a controller for receiving said first and second signals and for determining a value indicative of whether the magnitude of the second stream differs from the magnitude of the first stream. Means may be provided for terminating the flow of said first stream when the measured differential exceeds a preset value; e.g., the amount of fluid leaving the uterus is less than the amount entering by more than a selected value, thus indicating the patient is absorbing too much fluid. The present value will reflect the type of procedure being performed. The system may also include means for heating the first stream of fluid.

In one preferred embodiment, the apparatus is an open loop conduit system which circulates the liquid. The system includes a first fluid conduit for introducing a first stream of physiologically compatible fluid into the uterine cavity of a patient, as well as a second conduit for drawing away a second stream of said fluid from the uterine cavity. The system also includes means for measuring the magnitude of the first stream and producing a first electrical signal indicative thereof, as well as means for measuring the magnitude of the second stream and producing a second electrical signal indicative thereof. A controller is provided for receiving said first and second signals and using the magnitudes indicated thereby to calculate a value indicative of whether said second stream differs from said first stream by more than a preset value, thereby indicating absorption of fluid by the patient.

In a further embodiment of the system of the present invention, the term "magnitude" is defined as the weight of the fluid. The system further includes a source of the physiologically compatible fluid of a known weight which is in fluid communication with the first conduit for supplying said fluid to the uterus. A reservoir is disposed in fluid communication with the second conduit for receiving the fluid drained out the uterine cavity. The first and second measuring means are designed as electronic weight measuring devices (strain gauges, piezoelectric modules, etc.) which produce electronic signals proportionate to the weights of, respectively the source, and the reservoir. The signals are then fed to the controller, which totals the two weights and compares the total with the known initial weight of the source. If the total weights differ from the initial weight by more than a preset value, then the surgeon knows that the patient is absorbing too much liquid and may terminate the procedure.

Preferably, the source of fluid is disposed above the level of the patient and requires no pressurization or pumping other than gravity in order to flow into the uterus. The reservoir is disposed below the patient and, to assist in drawing the fluid from the uterus, a pump may be provided which is in operative association with the second conduit and the reservoir for pumping the fluid from the uterine cavity. Such a gravity fed system has a great advantage over prior art systems which actually pump the fluid into the uterine cavity (see, for example, Ankum, W., and J. Vonk, "The Spring Balance: a Simple Monitoring System for Fluid Overload During Hysteroscopic Surgery", *The Lancet*, volume 343, Apr. 2, 1994, pp 836-837). The prior art systems are inherently unsafe because the pressure in the uterus is basically uncontrollable. The pressure provided by the arrangement of the present system cannot exceed a certain maximum value which is determined by how high the source is disposed above the patient (typically 3 or 4 feet). By disposing the pump, which may be a suction pump or a peristaltic pump, downstream of the uterine cavity, the fluid is more readily drawn off, again increasing the safety factor because the pressure in the uterus drops as fluid is drawn out. In contrast, a pump disposed upstream of the uterus increases uterine pressure as it pumps. If such a pump malfunctions, it could even raise uterine pressure to the point of damage or rupture. If the downstream pump of the present invention were to malfunction, pressure in the uterus would merely drop with no adverse consequences.

As another safety precaution, the system may further include a valve disposed in said first conduit and in communication with the receiving means. The valve opens and closes to turn on or shut off the flow of fluid from the source to the uterus. The controller is further operative to close the valve when the difference between some of the weights of the source and the reservoir exceeds the initial weight of the source by more than the preset value.

In another aspect of the system of the present invention, the magnitude is defined as volume or flow rate, and the means for measuring comprises first and second devices for measuring volume or flow rate such as flow meters operatively associated with the first and second streams. The signals from these devices are fed to the controller which calculates a value representing the difference between the volumes measured for the first and second streams. The controller then compares this difference with a preset value. Thus, for example, if the flow rate going into the uterus exceeds the flow rate coming out of the uterus by more than the preset value, the surgeon knows that the patient is absorbing too much fluid and can terminate the procedure. This embodiment, like the embodiment described previously, can also include a valve disposed in the first conduit in communication with the controller for automatically stopping the flow of fluid into the uterus when the difference between the two flow rates exceeds the preset value.

BRIEF DESCRIPTION OF THE DRAWINGS

The following detailed description is best understood by reference to the drawings in which:

FIG. 3 shows an alternate arrangement of a fluid source useful in conjunction with the present invention.

DETAILED DESCRIPTION OF THE PREFERRED EMBODIMENT

Figure 1:
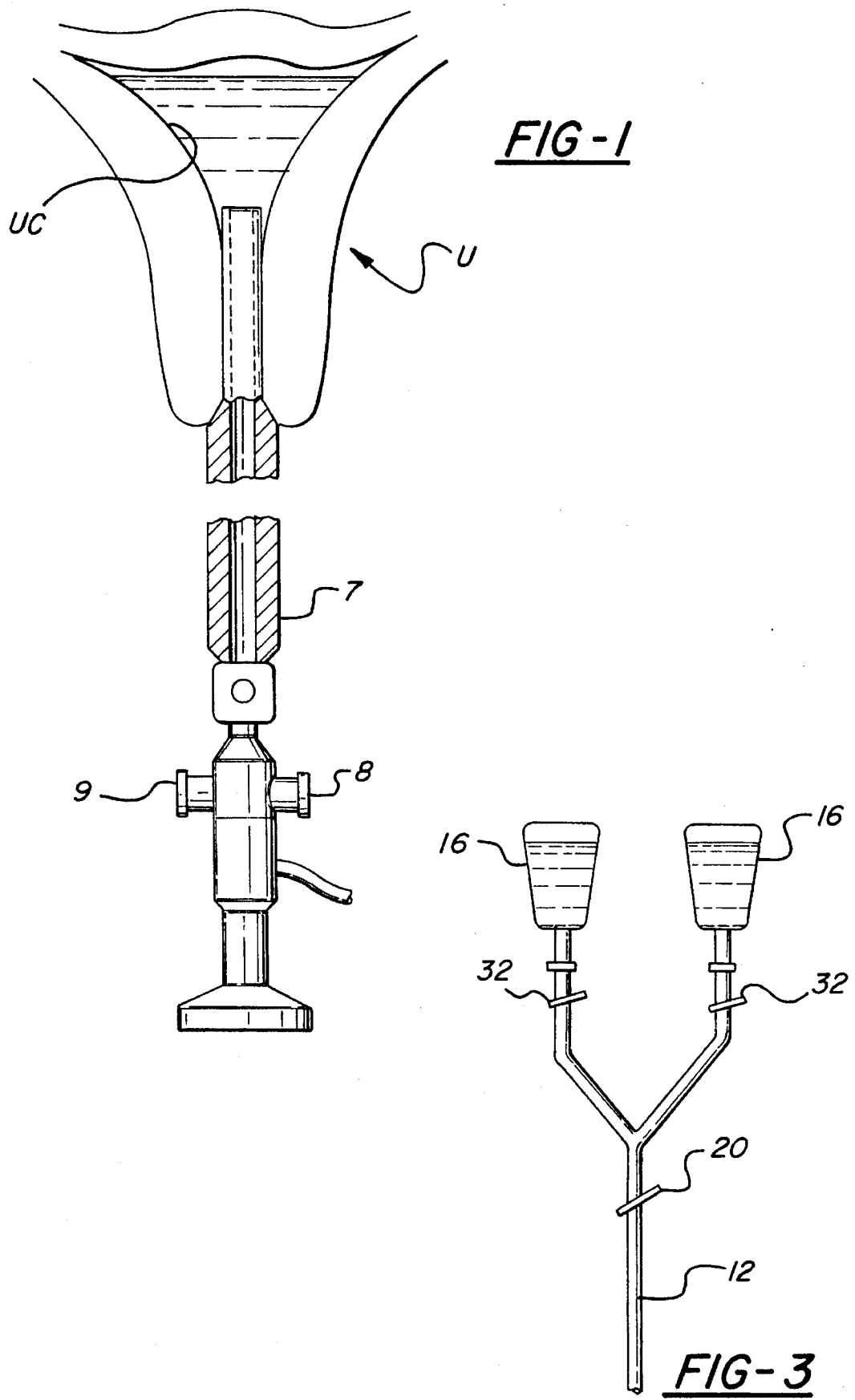
FIG. 1 is a schematic view of a hysteroscopic sheath used to perform endoscopic surgery of the uterus, said sheath being supplied with an inlet port and an outlet port.

Throughout the following detailed description, like numerals are used to reference the same element of the present invention shown in multiple figures thereof. Referring now to FIG. 1 there is shown a hysteroscopic sheath 7 suitable for practicing endoscopic surgical procedures on the uterus. Such procedures often require the continuous introduction of large amounts of fluid into the uterine cavity so as to expand the size thereof and give a clear view. Fluid from the uterine cavity UC then returns via the hysteroscopic sheath 7 (the fluid flow channels are not shown; reference is had to the '390 patent for a more complete description) and exits the sheath 7 via the exit port 9. Of course, the circulation system of the present invention is equally applicable for use with other types of hysteroscopes and interuterine cannulas.

Figure 2:
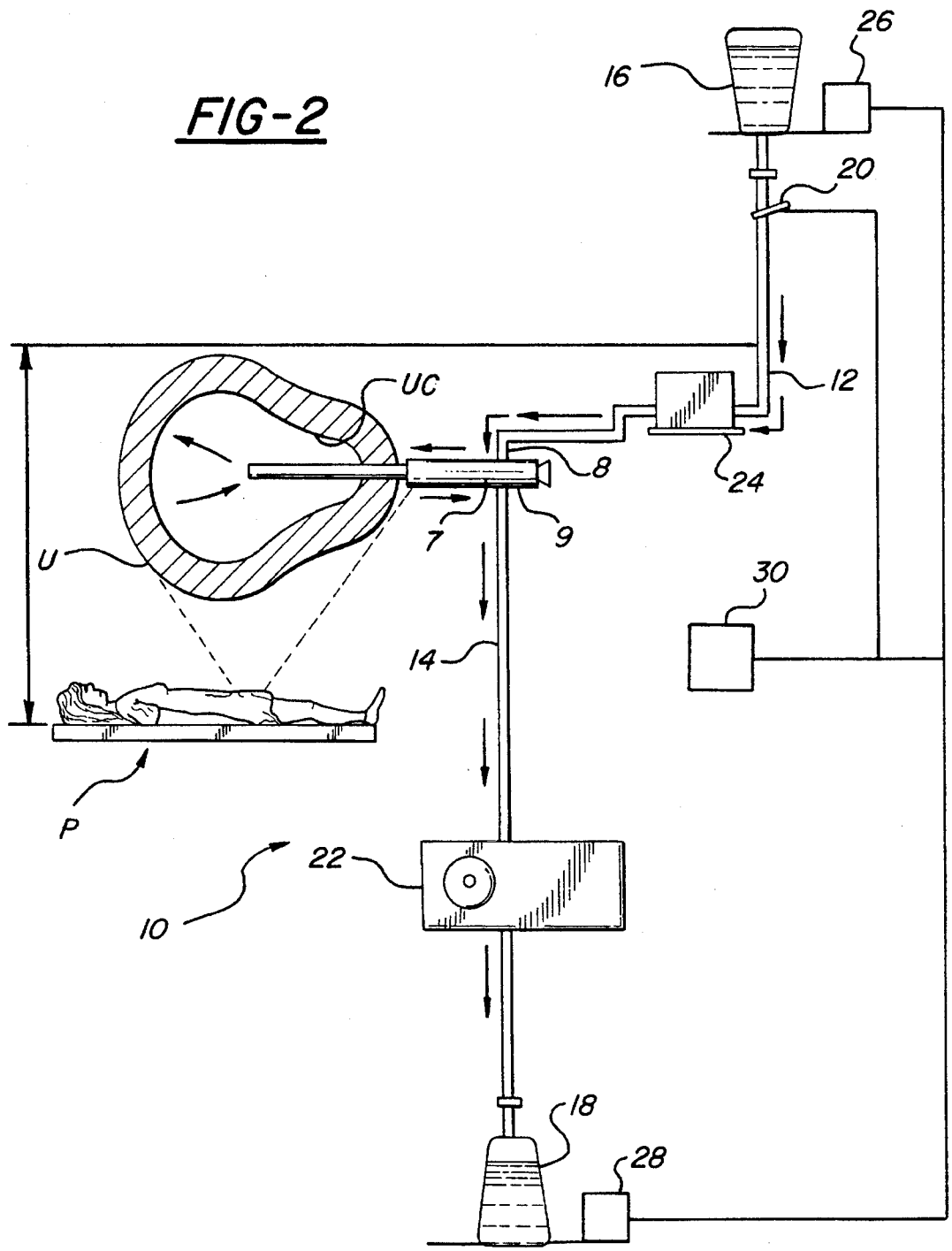
FIG. 2 is a schematic diagram of an open loop embodiment of the system of the present invention for supplying liquid to the hysteroscopic sheath of FIG. 1.

FIG. 2 depicts in schematic form such a hysteroscopic sheath 7 in use on a patient P. upon whom an endoscopic procedure is being performed. The present invention includes an apparatus 10 for circulating a quantity of a physiologically compatible fluid. In FIG. 2, the arrows show the direction of fluid flow through the various elements of the system 10. The system 10 includes a first conduit 12 for introducing physiologically compatible fluid into uterine cavity UC via inlet port 8. The system also includes a second conduit 14 for drawing fluid out of the uterine cavity UC via outlet port 9. A source of physiologically compatible fluid 16 is provided which is in fluid communication with the first conduit 12. Preferably, the source 16 is disposed several feet above the level of the patient P so that fluid will flow into the uterine cavity UC under the head of pressure created by gravity alone. A fluid reservoir 18 is in communication with the second conduit 14 for receiving fluid drained from the uterine cavity UC. Preferably, the reservoir 18 is disposed below the level of the patient and the flow of fluid out of the uterine cavity UC is assisted by means of pump 22 disposed along the second conduit 14.

A valve 20 is disposed in first conduit 12 so that the flow of fluid from source 16 may be started and stopped as the valve 20 opens and closes. Valve 20 is in communication with controller 30 which also communicates with a pair of measuring means 26, 28 in the form of electronic balances. Balance 26 weighs the amount of fluid in source 16, and balance 28 weighs the amount of fluid in reservoir 18. The balances 26, 28 generate, respectively, first and second signals indicative of the respective weights of source 16 and reservoir 18. These first and second signals are then fed to the controller 30. Optionally, a heater 24 may be disposed in conduit 12 for heating the liquid in certain procedures.

The embodiment 10 of the system of the present invention operates as follows. At the beginning of the procedure, the amount of fluid in the source 16 is weighed by balance 26 and that value is stored in the controller 30. The valve 20 is then opened to allow fluid to flow into the uterine cavity UC. The fluid expands the uterine cavity so that the surgeon can get a good view of the interior thereof. After the uterine cavity has expanded, fluid continues to flow thereinto and the excess is drawn out through second conduit 14 with the assistance of pump 22. Subsequently, it flows into reservoir 18. The weight of the fluid in reservoir 18 is continuously weighed via balance 28, as is the amount of fluid in the source 16. The respective weights of the source 16 and the reservoir 18 are then totalled by the controller and compared with the initial weight of fluid stored therein. Also stored in controller 30 is a preset value which represents an expected differential which takes into consideration the nature of the surgery and the amount of unweighable fluid (in the uterine cavity, in the sheath, etc.). This preset value will differ for different procedures; i.e., in the case where the fluid is not heated, the patient can safely absorb a considerable larger quantity of fluid than is the case with a heated liquid. The controller then compares the differential between the total weights of the fluid in source 16 and reservoir 18 and the initial amount of fluid with the preset value. If the preset value is exceeded, the controller sends a signal to the valve 20 to stop the flow of fluid.

Alternatively, the initial weight of the source fluid could be determined after the system has been primed; i.e., after fluid has flowed into the uterus and has begin to flow therefrom. In that case, the total of the weights of the fluid in the source and in the reservoir as the procedure is being performed should approximately equal the initial weight of the source. The preset value stored in the controller will then be smaller since it will not have to take into account unweighable liquid in the system.

Of course, it is to be understood that measuring means 26, 28 could be other than electronic balances and could measure other values than the weight of the fluid. For example, they could be devices to measure the volumes or flow rates of the fluid passing through the first and second conduits. A device such as a flow meter would send signals to the controller indicative of the amount of fluid flowing through the conduit. In this case, the controller would be programmed somewhat differently than in the embodiment previously described. Rather than totalling the values sent by the measuring means 26, 28, the controller would determine a difference between them and compare that difference with a preset value stored therein. That is, if the volume or flow rate in the second conduit is significantly less than the volume or flow rate in the first conduit, the surgeon will know that the patient is absorbing too much fluid. Again, the controller 30 will then send a signal to the valve 20 to close it to stop flow of fluid into the uterine cavity.

FIG. 3 illustrates an alternative arrangement of the source of physiological compatible fluid used with the apparatus of the present invention. In this case, two sources 16 are provided which are hooked in tandem. Many hysteroscopic procedures require the introduction of larger volumes of fluid into the uterine cavity then can be easily accommodated in a single fluid bag or bottle. In the arrangement shown in FIG. 3, each source 16 is provided with its own valve 32 so that, as soon as one empties, the other one may be started.

The fluid circulation system of the present invention may be used to deliver either cold or heated fluid to the uterine cavity as required by the particular surgical procedure involved. Since it is not a closed loop system, it is capable of delivering a continuous flow of clear, clean fluid, and yet provides continuous monitoring to ensure the safety of the patient. Furthermore, because the system does not use a pump upstream of the uterine cavity, it is much safer than prior art systems. Additionally, because it is an electronic based system, it is capable of continuous monitoring.

The system of the present invention has been described with reference to certain embodiments and exemplifications thereof. Doubtless, a skilled artisan having the benefit of the teachings of the present disclosure may design other variations which do not depart from the scope of the present invention. For example, while the system has been described with reference to devices for measuring weight, volume and flow rate, it is possible that it may utilize other types of measuring devices which measure other quantifiable physical parameters, such as, for example, fluid pressure. Thus, the present invention is not limited to the exact embodiments and exemplifications depicted but, rather, by the claims appended hereto and all reasonable equivalents thereof.

I claim:

1. A fluid delivery system for use in hysteroscopic procedures requiring the delivery of a fluid to the uterine cavity of a patient, said system comprising:

a first conduit disposed above the level of said patient for introducing by gravity flow a first stream of physiologically compatible fluid into the uterine cavity of a patient;

a second conduit disposed below the level of said patient for drawing away by gravity flow a second stream of said fluid from said uterine cavity;

means for measuring a first quantity of fluid in said first stream flowing into said uterine cavity and producing a first electrical signal indicative thereof;

means for measuring a second quantity of fluid in said second stream drawn out of said uterine cavity and producing a second electrical signal indicative thereof; and a controller for receiving said first and second signals and calculating on the basis of the first and second quantities indicated thereby a value indicative of whether said second stream differs from said first stream by more than a preset value reflecting a maximum permissible amount of fluid which said patient may safely absorb, thereby indicating absorption of said fluid by the patient.

2. The system of claim 1 wherein said calculated value is a difference between said first and second quantities and said receiving means is further operative to compare said difference with said preset value.

3. The system of claim 2 wherein said quantities is defined as flow rate, and said means for measuring comprises flow meters strain gauges operatively associated with, respectively, said first and second fluid streams.

4. The system of claim 2 wherein the quantities is defined as volume.

5. The system of claim 1 further comprising a source of said physiologically compatible fluid of a known initial quantity and in fluid communication with said first conduit, wherein said calculated value is a sum of said first and second quantities, said controller being further operative to determine the difference between said sum and the known initial quantity of said source of fluid, and to compare said difference with said preset value.

6. The system of claim 5 wherein said quantities is defined as weight and said means for measuring comprises first and second electronic balance.

7. The system of claim 5 further comprising
means for terminating the flow of said first stream when said difference exceeds a preset value.

8. The system of claim 1 further comprising means for heating said first stream of liquid.

9. The system of claim 1 further comprising a pump operatively associated with said second conduit for pumping said second stream of liquid out of the uterine cavity.

10. The system of claim 9 further comprising a valve for opening and closing said first conduit and a switch in communication with said controller for closing said valve when said calculated value exceeds said preset value.

11. A fluid delivery system for use in hysteroscopic procedures requiring the delivery of a fluid to the uterine cavity of a patient, said system comprising:

a source of physiological compatible liquid of a known initial weight disposed above the level of a patient undergoing an hysteroscopic procedure;

first means for continuously measuring the weight of said liquid remaining in said source;

a first conduit in fluid communication with said source for introducing unpressurized physiologically compatible liquid into the uterine cavity of said patient;

a second conduit for drawing physiological compatible liquid away from said uterine cavity;

a fluid reservoir disposed below the level of said patient and in fluid communication with said second conduit for receiving physiologically compatible liquid drawn out of said uterine cavity;

second means for continuously measuring the weight of said liquid in said reservoir;

a pump operatively associated with said second conduit for pumping physiologically compatible liquid from said uterine cavity; and a controller in communication with said first and second measuring means for determining the sum of the weights thereof and comparing said sum with said known initial weight of said source to calculate a differential therebetween.

12. The system of claim 11 wherein said controller is further operative to compare said differential with a preset value reflecting a maximum permissible amount of fluid which said patient may safely absorb 13. The system of claim 12 further comprising a valve for opening and closing said first conduit, said valve being in communication with said controller, said controller being further operative to close said valve when said differential exceeds said preset value.

* * * * *